(12) United States Patent
de la Torre Garcia et al.

(10) Patent No.: US 6,528,492 B1
(45) Date of Patent: Mar. 4, 2003

(54) SINGLE-STEP PROCESS FOR PREPARING 7, 16-DEOXY-2-AZA-10-0-CLADINOSIL-12-0-DESOSAMINIL-4, 5-DIHYDROXY-6-ETHYL-3, 5,9,11,13,15-HEXAMETHYLBICYCLE (11.2.1) HEXADECA-1(2)-EN-ONA AND OBTAINING A NEW FORM OF 9-DEOXO-9A-METHYL-9A-AZA-9A-HOMOERYTHROMYCIN A

(75) Inventors: Juan Antonio de la Torre Garcia, Jiutepec Mor (MX); Fidencio Franco Andrade, San Pedro Xalpa (MX); Jose Manuel Francisco Lara Ochoa, De Coyoacan (MX)

(73) Assignees: Instituto de Investigacion en Quimica Aplicada S.C. (MX); Silanes S.A. de C.V. (MX)

( * ) Notice: Subject to any disclaimer, the term of this patent is extended or adjusted under 35 U.S.C. 154(b) by 0 days.

(21) Appl. No.: 09/673,021

(22) PCT Filed: Jul. 25, 2000

(86) PCT No.: PCT/MX00/00030

§ 371 (c)(1), (2), (4) Date: Sep. 20, 2001

(87) PCT Pub. No.: WO02/10144

PCT Pub. Date: Feb. 7, 2002

(51) Int. Cl.[7] ............ A61K 31/70; C07H 1/00; C07H 17/08
(52) U.S. Cl. ............ 514/29; 536/7.4; 536/18.5
(58) Field of Search ............... 536/7.5, 18.5; 514/29

(56) References Cited

U.S. PATENT DOCUMENTS

| | | | |
|---|---|---|---|
| 3,478,014 A | 11/1969 | Djokic etal. | 260/210 |
| 4,328,334 A | 5/1982 | Kobrehel et al. | 536/7.4 |
| 4,474,768 A | 10/1984 | Bright | 424/180 |
| 4,517,359 A | 5/1985 | Kobrehel et al. | 536/7.4 |
| 4,963,531 A | 10/1990 | Remington | 514/29 |
| 5,605,889 A * | 2/1997 | Curatolo et al. | 514/29 |
| 5,686,587 A | 11/1997 | Yang | 536/7.1 |
| 6,245,903 B1 | 6/2001 | Karimian et al. | 536/7.4 |
| 6,268,489 B1 | 7/2001 | Allen et al. | 536/7.4 |

FOREIGN PATENT DOCUMENTS

| | | |
|---|---|---|
| EP | 0 879 823 A1 | 11/1998 |
| WO | WO 99/58541 | 11/1999 |
| WO | WO 01/00640 A1 | 1/2001 |
| WO | WO 02/09640 A2 | 2/2002 |
| WO | WO 02/15842 A2 | 2/2002 |

OTHER PUBLICATIONS

Tamura, Y. et al., *Tetrahedron Lett.*, 40:4133–4135 (1972).
Djokic, S. et al., *J. Chem. Res.*, 152–153 (1988).
Bayod–Jasanada, M. et al., *J. Org. Chem.*, 62:7479–7481 (1997).

* cited by examiner

*Primary Examiner*—Elli Peselev
(74) *Attorney, Agent, or Firm*—Sterne, Kessler, Goldstein & Fox P.L.L.C.

(57) ABSTRACT

Improved single-step process for preparing 7,16-deoxy-2-aza-10-O-cladinosyl-12-O-desosaminyl-4,5-dihydroxy-6-ethyl-3,5,9,11,13,15-hexamethylbicycle[11.2.1]hexadeca-1(2)-en-8-ona from erythromycin A, with high yield and under soft conditions suitable for its industrial production. The transformation of erythromycin A into an intermediate compound, called 6,9-iminoether, which is obtained in a single step, is achieved by forming the mesitylenesulfonyloxime "in situ" from erythromycin, which in the presence of a base in aqueous acetone undergoes a Beckmann's transposition creating the iminoether with the help of the hydroxyl in position 6 of the macrolide ring; this intermediary is transformed into the antibiotic 9-deoxo-9a-methyl-9a-aza-9a-homoerythromycin A, which is obtained by precipitation in hexane, thereby obtaining an innovative form, with an anhydrous crystalline structure and physical characteristics different from the forms known to date.

14 Claims, 9 Drawing Sheets

Azithromycin

SINGLE-STEP PROCESS FOR PREPARING 7, 16-DEOXY-2-AZA-10-0-CLADINOSIL-12-0-DESOSAMINIL-4, 5-DIHYDROXY-6-ETHYL-3, 5,9,11,13,15-HEXAMETHYLBICYCLE (11.2.1) HEXADECA-1(2)-EN-ONA AND OBTAINING A NEW FORM OF 9-DEOXO-9A-METHYL-9A-AZA-9A-HOMOERYTHROMYCIN A

FIELD OF THE INVENTION

This invention comprises forming an intermediate product called 6,9 iminoether in a single step from erythromycin, which is transformed into a new and useful form of azithromycin, which is recovered by means of precipitation in hexane.

BACKGROUND OF THE INVENTION

The antibiotic [2R-(2R*, 3S*, 4R*, 5R*, 8R*, 10R*, 11R*, 12S*, 13S*, 14R*)]-13-[(2,6-Dideoxy-3-C-methyl-3-O-methyl-α-L-ribo-hexopyranosyl)oxy]-2-ethyl-3,4,10-trihydroxy-3,5,6,8,10,12,14-heptamethyl-11-[[3,4,6-trideoxy-3-(dimethylamino)-β-D-xylo-hexopyranosyl]oxy]-1-oxa-6-azacyclopentadecan-15-one, or IUPAC name 9-deoxo-9a-methyl-9a-aza-9a-homoerythromycin A, and generic name azithromycin is a broad-spectrum bactericide derived from erythromycin A. It differs structurally from erythromycin A due to the insertion of a methylated nitrogen moiety in position 9a in the lactone ring to create a 15-member macrolide. The structural modification significantly improves the antibiotic's effectiveness against defective cell wall bacteria such as Mycoplasma pneumoniae, Chlamydia trachomatis, Chlamydia pneumoniae, etc. or the complex Mycobacteria avium, and achieves higher concentrations in the organism.

Azithromycin was discovered by Kobrehel et al. and first patented in Yugoslavia under number P592/81, and subsequently in Belgium under number 892357, under the name N-methyl-11-aza-10-deoxy-10-dihydroerythromycin A. The reaction sequence reported in the literature used to transform erythromycin A (1) into azithromycin (5) includes 4 principal steps, illustrated in FIG. 1, which are described in general terms below.

a) Formation of Oxime (2)

The oxime is formed from erythromycin A (1) by means of reaction with hydroxylamine hydrochloride in methanol.

b) Beckmann's Rearrangement of the Oxime (2)

The intramolecular participation of the neighboring 6-hydroxy group is observed when Beckmann's rearrangement is carried out at 0° C. with p-toluenesulfonyl chloride in aqueous acetone, producing the 6,9-iminoether (3). This iminoether (3) and the process used to obtain it have been described in worldwide patent 26,758, and European patent 0,137,132. In U.S. Pat. No. 4,328,334, this iminoether is erroneously assigned to the structure of a lactam obtained using Beckmann's rearrangement from the oxime of erythromycin A (1).

c) Reduction of the Iminoether (3)

Reduction of the iminoether (3) to the secondary amine (4) with sodium borohydride in methanol (*J. Chem. Soc. Perkin Trans.* 1, 1986, 1881; *J. Org. Chem.* 1997, 62, 7479–7481) or by catalytic hydrogenation in the presence of platinum dioxide and acetic acid as solvents (*Tetrahedron Lett.* 1994, 35, 3025).

d) Reductive Methylation of the Secondary Amine (4) to Obtain Azithromycin (5)

This process is described in U.S. Pat. No. 4,517,359, and in *J. Chem. Res.* 1988, 132. It consists basically of the Escheweiler-Clarke reaction and uses formaldehyde in acetic acid or formaldehyde, and formic acid in carbon tetrachloride or chloroform for methylation (FIG. 1). The main difficulty with these reactions, as they are described, is the formation of certain impurities such as formamide, derived from the amine 9-deoxy-9a-aza-9a-homoerythromycin A.

Recently, an alternative method was described in which the iminoether (3) can be reduced and the product obtained subsequently submitted to reductive methylation in the presence of formaldehyde with a noble metal as catalyst, without the need to isolate the intermediary (FIG. 1). Under these conditions, we obtain azithromycin with high purity and good yield in a single step from the iminoether (3) (European patent 0,879,823 A1).

Studies to elucidate the structure of azithromycin have brought to light two crystalline forms corresponding to the monohydrate and dihydrated forms (PCT/US87/01612, and *J. Chem. Res.* 1988, 132). Patent PCT/US87/01612 attributes to the azithromycin patented by Kobrehel et al. (Yugoslav patent P592/81, Belgian patent 892357 and U.S. Pat. No. 4,517,359) to correspond with the amorphous form.

This invention is intended to offer an alternative to known methods, in order to form the intermediary 6,9-iminoether in a single step from erythromycin to obtain 9-deoxo-9a-methyl-9a-aza-9a-homoerythromycin A, which is an evident improvement on existing preparation methods.

A further purpose of this invention is to prepare a novel form of 9-deoxo-9a-methyl-9a-aza-9a-homoerythromycin A with physical characteristics different from those detected thus far. B1

DESCRIPTION OF THE INVENTION

Figure 1:
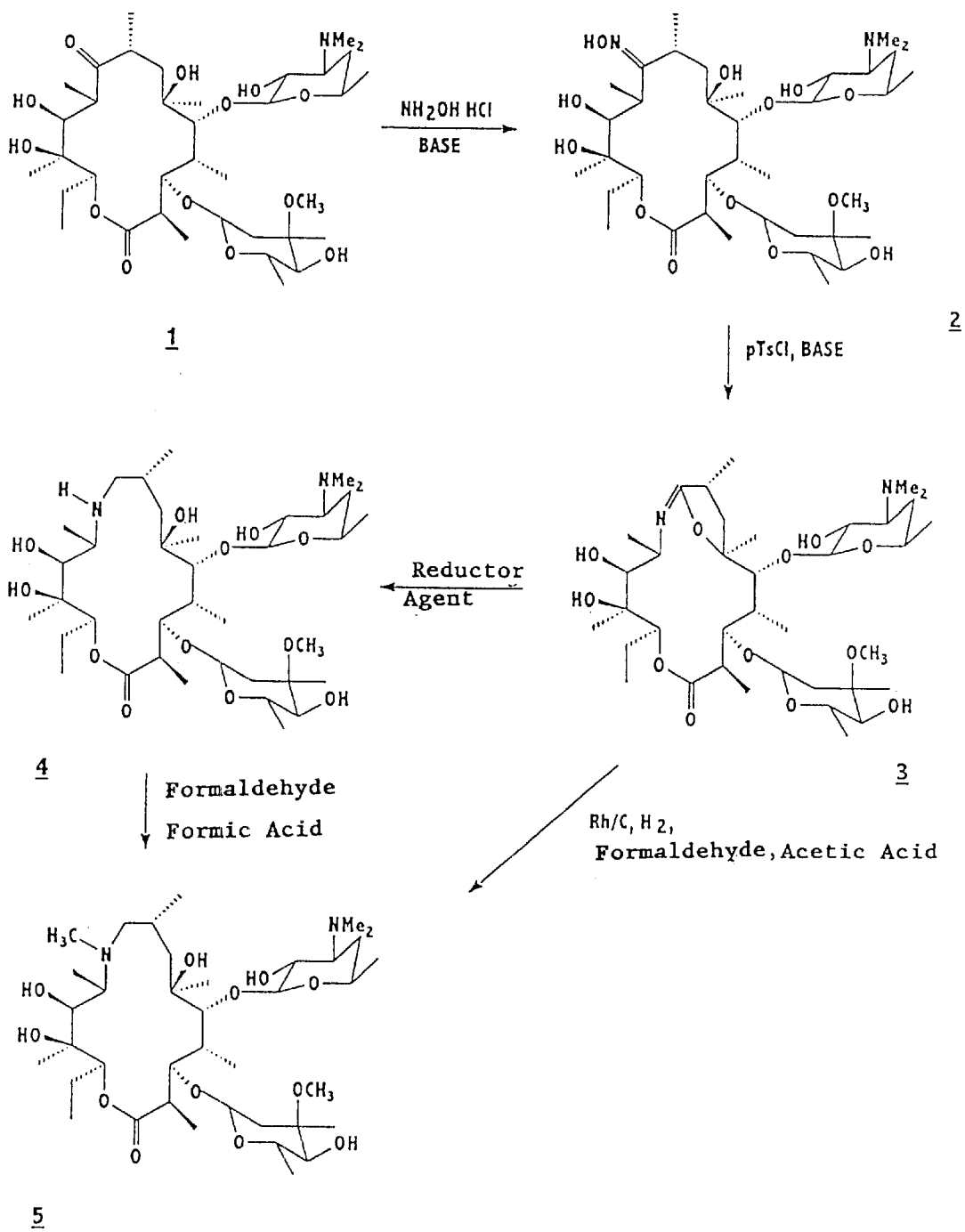
FIG. 1 depicts methods reported to date for preparing azithromycin.
Figure 2:
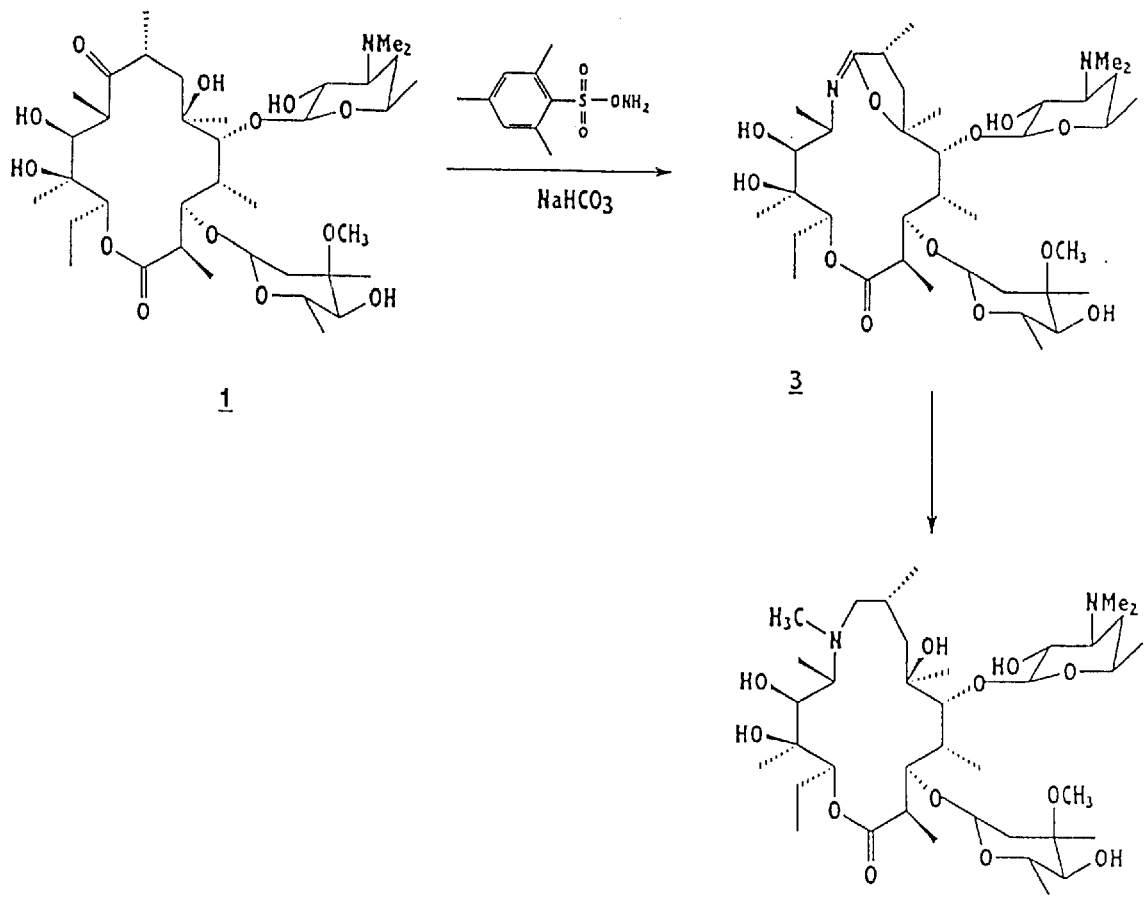
FIG. 2 depicts the azithromycin process of the invention.

All the methods reported to date for preparing azithromycin (5) involve the formation of the oxime (2) from erythromycin A (FIG. 1) by treating the erythromycin in methanol with hydroxylamine hydrochloride and a base at reflux temperature for at least 10 hours. This oxime is isolated, purified and subsequently subjected to Beckmann's rearrangement to obtain the intermediary (3) (FIG. 1) in aqueous acetone in the presence of p-toluenesulfonylchloride and base for 2 hours at 5° C. and 2 hours more at room temperature. The innovative aspect of this invention is that the iminoether (3) is prepared in a single step (FIG. 2) from erythromycin A (1), which is operatively and economically more feasible than the aforementioned methods. The reaction described in this invention consists of treating an erythromycin A (1) solution in acetone with O-mesitylenesulfonylhydroxylamine (MSH), to form the mesitylenesulfonyloxime "in situ" from erythromycin A, which, on being treated with an aqueous base (sodium bicarbonate) at 0° C., undergoes a Beckmann's rearrangement, giving rise to the intermediary 6–9-iminoether (3) (FIG. 2). Reaction conditions are soft, with short times and the reactive used in this transformation (MSH) is easily prepared as described in *Tetrahedron lett.* No. 40, p. 4133–4135 (1972). Also, the method described in this invention is scalable for industrial production. After preparing the intermediary (3) (FIG. 2), it is possible to obtain azithromycin (5) by means of catalytic reduction followed by reductive methylation using common techniques described in the literature (see for example M. Hudlický, Reductions in Organic Chemistry $^2$nd ed., ACS monograph 188, 1996 or S. H. Pine and B. L. Sánchez, J. Org. Chem. 36, 829–832 (1971).

The procedure for producing the intermediate compound (3), called 7,16 deoxy-2-aza-10-O-cladinosyl-12-O-disosaminyl-4,5-dihydroxy-6-ethyl-3,5,9,11,13,15-hexamethylbicyclo[11,2,1]hexadeca-1(2)-en-8-ona is described below, using the following example:

EXAMPLE 1

Figure 3:
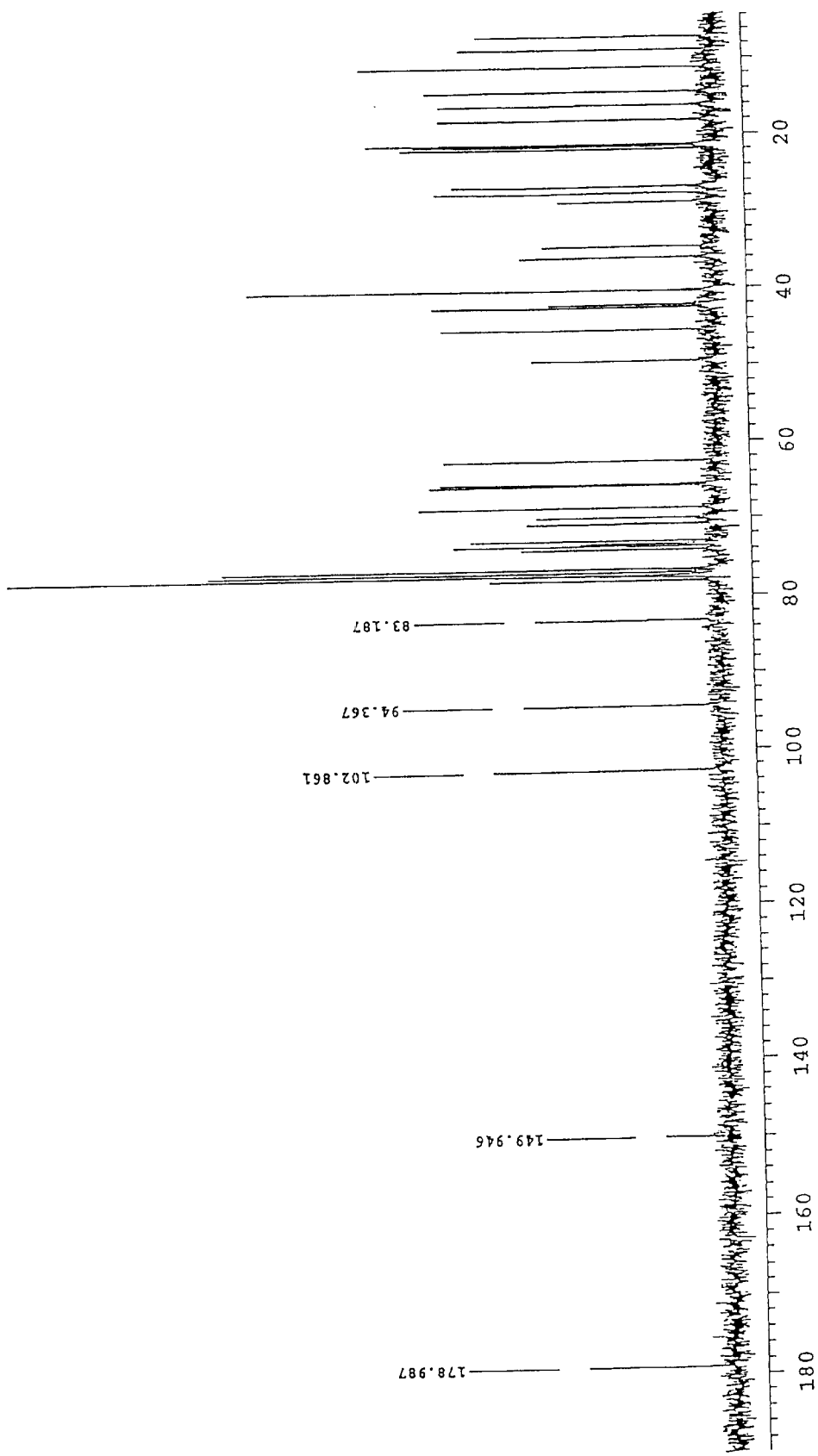
FIG. 3 depicts the $^{13}$C NMR spectrum of the crystalline anhydrous azithromycin of the invention.
Figure 4:
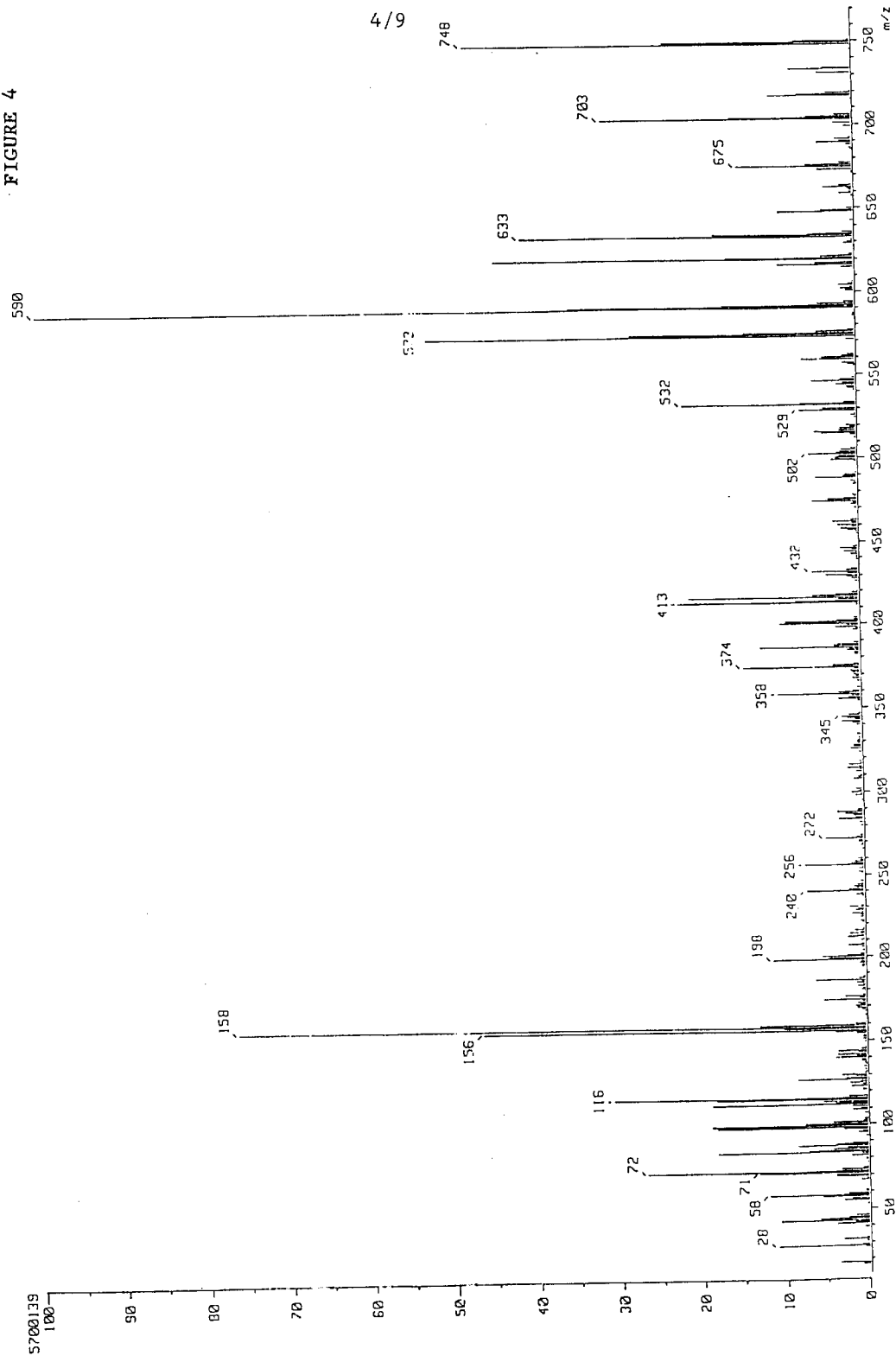
FIG. 4 depicts a mass spectrum of the crystalline anhydrous azithromycin of the invention.

A solution of erythromycin A (6.0 g, 0.082 mol) in 30 ml of acetone, in an $N_2$ atmosphere was cooled to 0° C., and 1.62 g (1.05 eq) of O-(mesitylenesulfonyl) hydroxylamine (MSH) was added. Agitation was continued at 0° C. for 5 minutes and the temperature was allowed to rise to room temperature, continuing agitation for one hour more. Thereafter the reaction mixture was again cooled to 0° C., and a solution of 2.75 g (0.032 mol) of sodium bicarbonate in 30 ml of water was added drop by drop, maintaining the internal temperature between 0 and 5° C.; the addition time was 30 minutes, and having finished adding the aforementioned solution the temperature was allowed to rise to room temperature and the mixture was agitated for additional 2 hours. Finally, the acetone was evaporated under low pressure and the aqueous residue was adjusted to a pH of 5.5 with HCl 2N. This phase was extracted twice with $CH_2Cl_2$ (20 ml). Extraction was repeated at pH of 6.0 (2×20 ml) and finally at pH 8.0 (3×20 ml). The pH 8.0 extracts were dried with potassium carbonate and evaporated to dryness, obtaining 4.48 grams (75%) of compound (3). The iminoether (3) obtained was reduced by catalytic hydrogenation in Raney nickel W6 which contains 10% to 11% aluminum, under pressure of 85 bars. The cyclic amine obtained was isolated and dissolved in methylene chloride to be subjected to reductive methylation using formic acid at 88%, formaldehyde at 33% and sodium formiate (S. H. Pine and B. L. Sánchez, J. Org. Chem. 36, 829–832 (1971)). The reaction takes place at 80° C. and lasts 24 hours. At the end of the reaction, pH is adjusted to 8 with NaOH and the organic phase is separated. The aqueous layer is extracted several times with methylene chloride, the extracts are combined with the organic layer, the mixture is dried with a drying agent such as sodium sulfate, the methylene chloride is evaporated and the solid obtained is rinsed with water and oven dried. The solid is dissolved in hexane and, under appropriate reflux conditions, precipitates a white crystalline solid which, by means of $^{13}$C nuclear magnetic resonance and mass spectrometry, is identified as the compound 9-deoxo-9a-methyl-9a-aza-9a-homoerythromycin A. Chemical shifts characterizing the $^{13}$C(CDCl$_3$) spectrum are as follows: 178.9 ppm, 149.9 ppm, 102.8 ppm, 94.3 ppm, 83.18 ppm (the spectrum is shown in FIG. 3). The molecular weight determined by mass spectrometry is 748, and the fragmentation pattern is consistent with that of a 9-deoxo-9a-methyl-9a-aza-9a-homoerythromycin A molecule (the mass spectrum is shown in FIG. 4).

Figure 5:
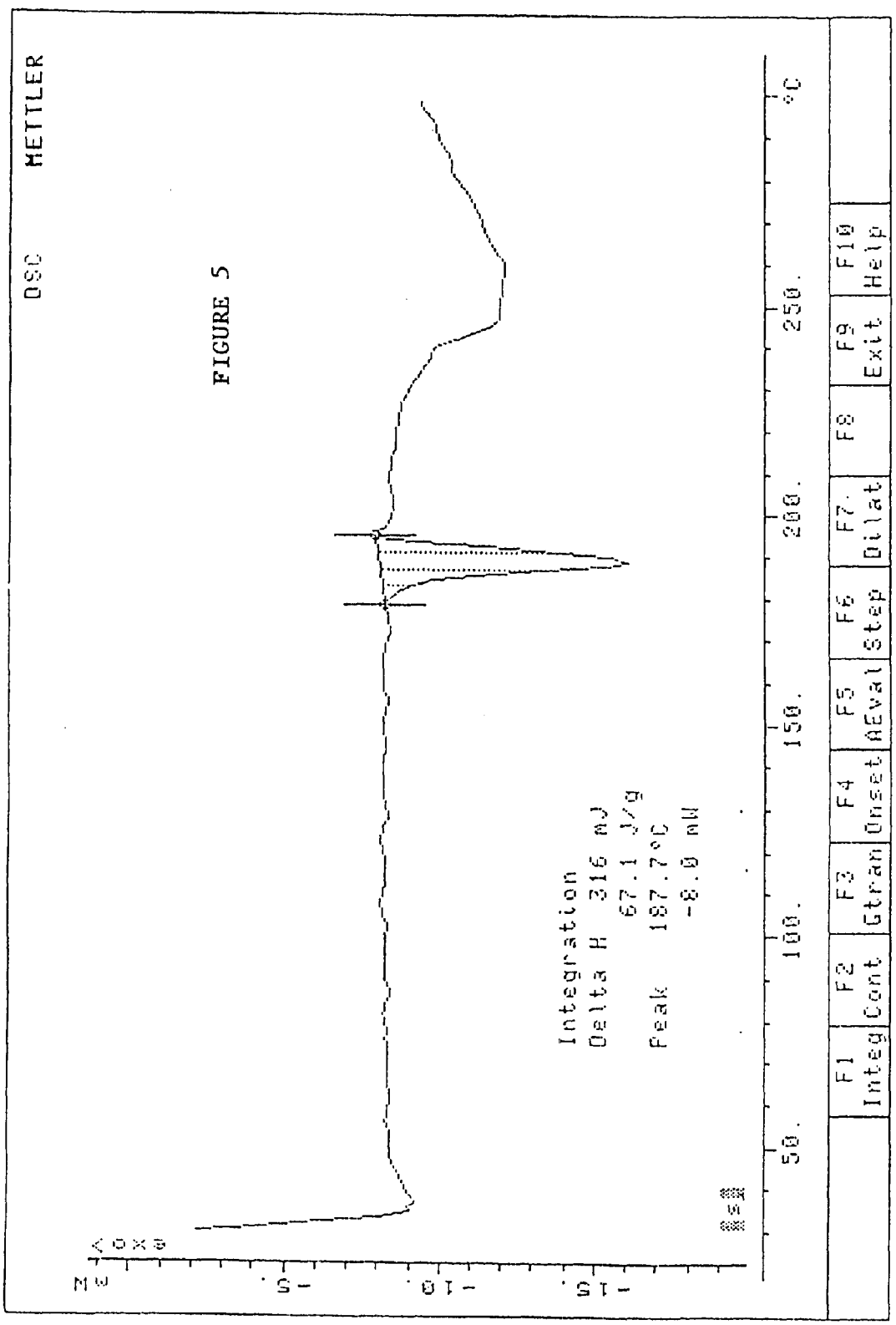
FIG. 5 depicts a graph of the Scanning Differential Thermal Analysis of the crystalline anhydrous azithromycin of the invention.

The melting point of the crystal, determined by the Fisher Jones method, is 188° C. to 189° C. Using Scanning Differential Thermal Analysis, it is obtained an endotherm at 187.70° C. The corresponding graph is shown in FIG. 5. Calculating specific rotation gives a value of −0.36 (1% in CHCl$_3$). These parameters are clearly different from the values found for other forms of azithromycin patented to date. Thus, we find that the azithromycin reported by Kobrehel et al. (Yugoslav patent 592/81, Belgian patent 892357, U.S. Pat. No. 4,517,359, Mexican patent 9100364) has a melting point from 113° C. to 115° C. and its specific rotation is −37.0 (1% in CHCl$_3$). The azithromycin patented by Bright (U.S. Pat. No. 4,747,668) has a melting point of 142° C. (in recrystalized form), and the dihydrated crystalline azithromycin has a melting point of 125° C. and a specific rotation of −41.4 (1% in CHCl$_3$) (Patent PCT/US87/0612, and Mexican patent 176627).

Figure 6:
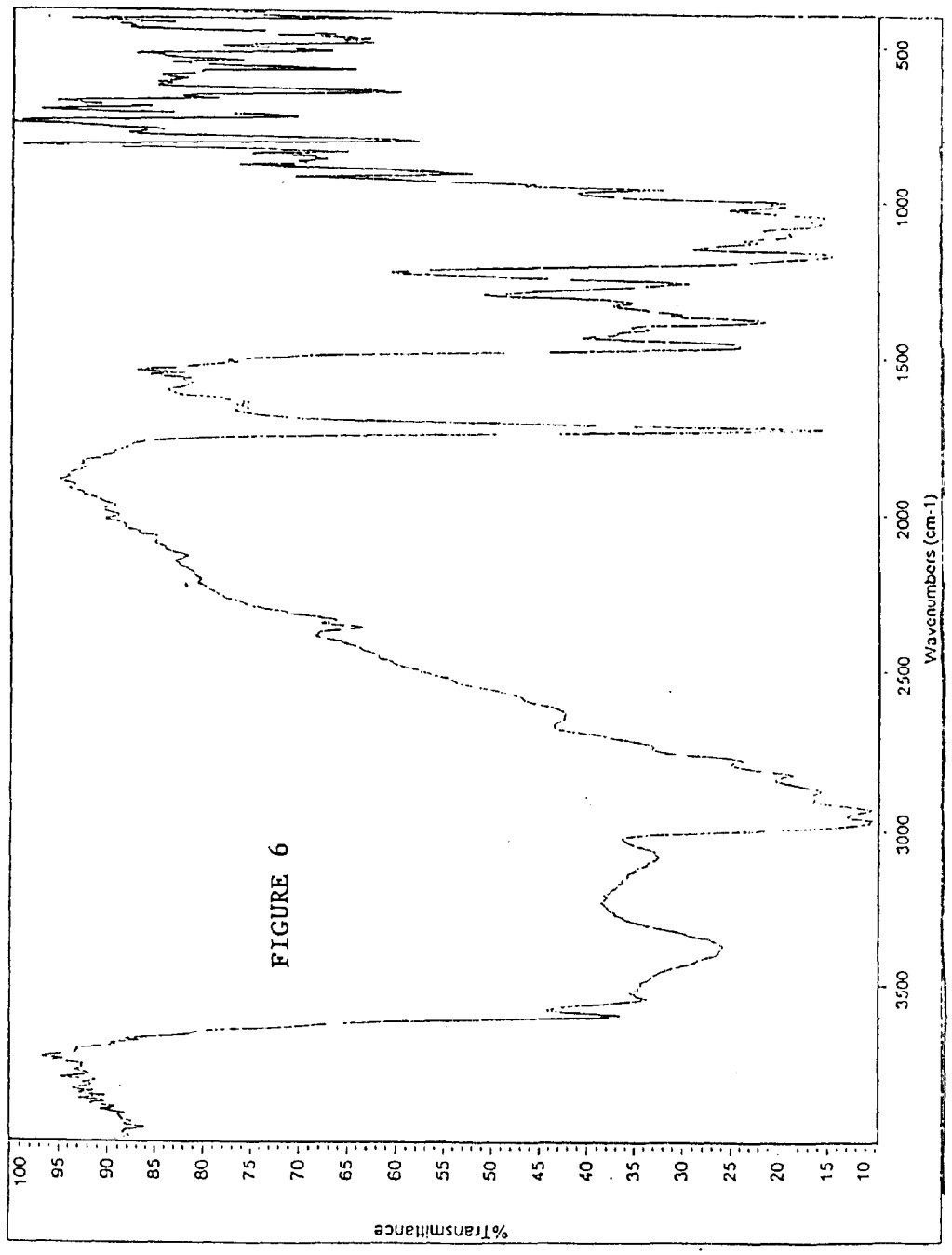
FIG. 6 depicts an infrared absorption spectrum of the crystalline anhydrous azithromycin of the invention.

The new crystal's infrared spectrum shows four medium intensity signals in the 3000 cm$^{-1}$ to 3700 cm$^{-1}$ region, located at approximately 3600 cm$^{-1}$, 3553 cm$^{-1}$, 3375 cm$^{-1}$, and 3075 cm$^{-1}$. On the contrary, it does not display the intense signal reported for the dihydrated form (Patent PCT/US87/01612) located at 3488 cm$^{-1}$, or those located at 2089 cm$^{-1}$ and 1644 cm$^{-1}$. In contrast, the new crystal's spectrum shows two signals around 2365 cm$^{-1}$. The infrared spectrum of the crystal obtained is shown in FIG. 6.

Figure 7:
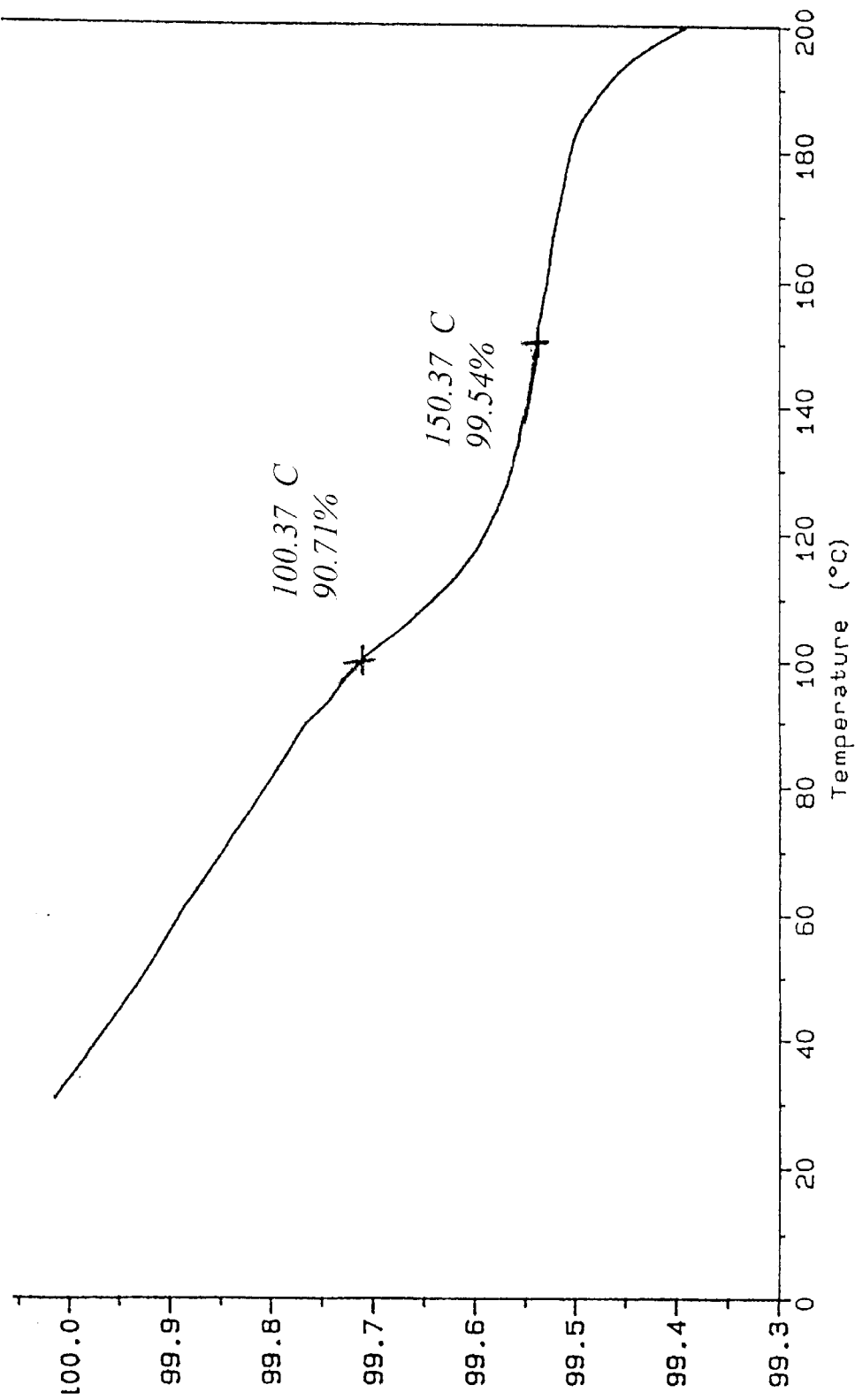
FIG. 7 depicts the results of a thermogravimetric analysis of the crystalline anhydrous azithromycin of the invention.

Calculating the amount of water present in the new crystal using Karl Fisher's method gives us a value of 0.65%. Using thermogravimetric analysis we obtain a weight loss equal to 0.6% by heating to 200° C. at a rate of 30° C. per minute. FIG. 7 shows the graph obtained using this method. These results indicate that the water present in the sample corresponds to moisture absorbed from the atmosphere but not hydration water (defined as water molecules that form part of the crystalline network), as the theoretical minimum corresponding to a hydration water molecule will be 2.35% of its total weight. This conclusion that the detected water correspond only to moisture is corroborated by the elemental analysis of the sample, obtaining the ratio: C 60.59%, H 10.06%, N 3.65%, O 25.77%, which coincides with condensate formula $C_{38}H_{72}N_2O_{12}$.

Figure 8:
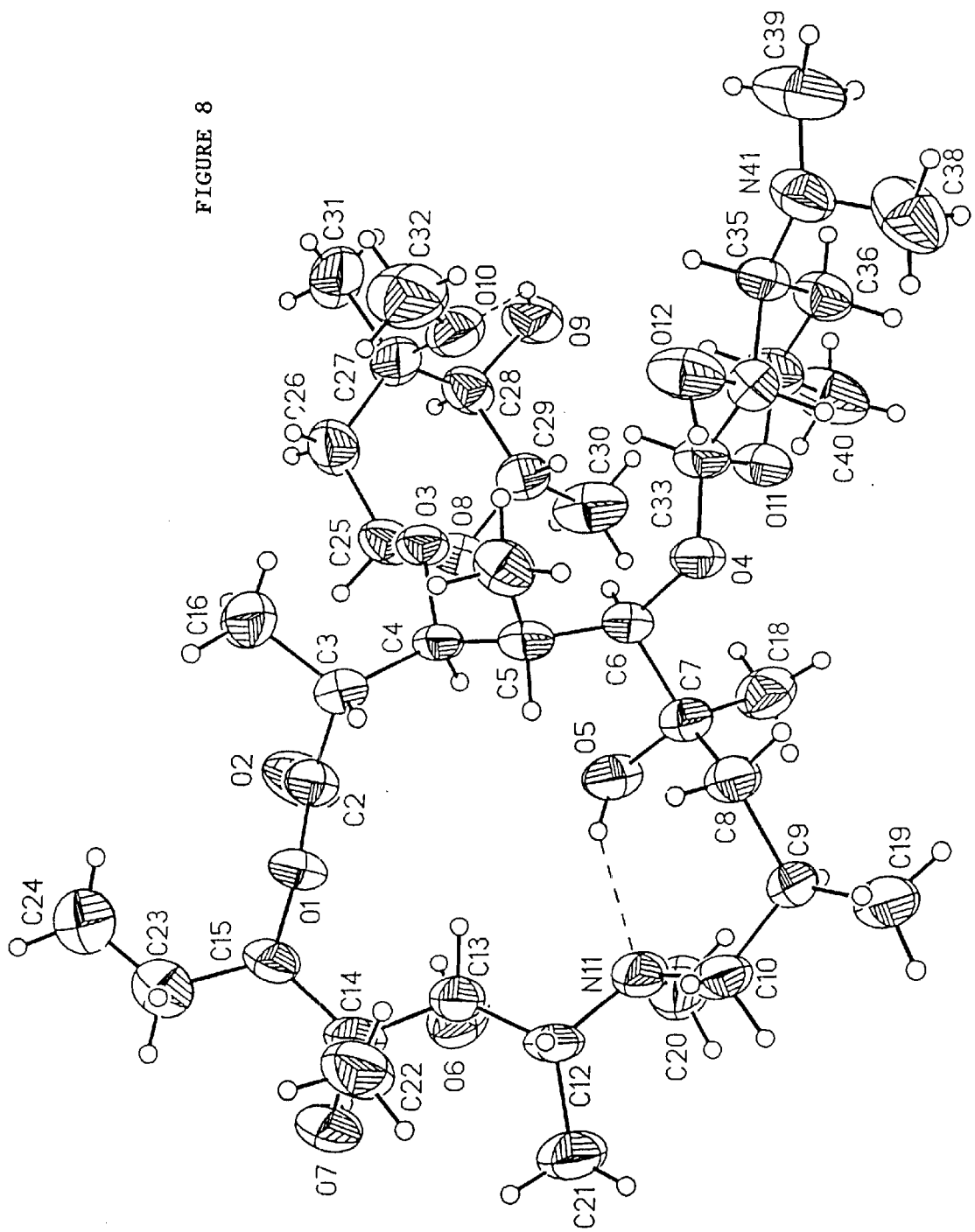
FIG. 8 depicts an x-ray crystal structure of the crystalline anhydrous azithromycin of the invention.
Figure 9:
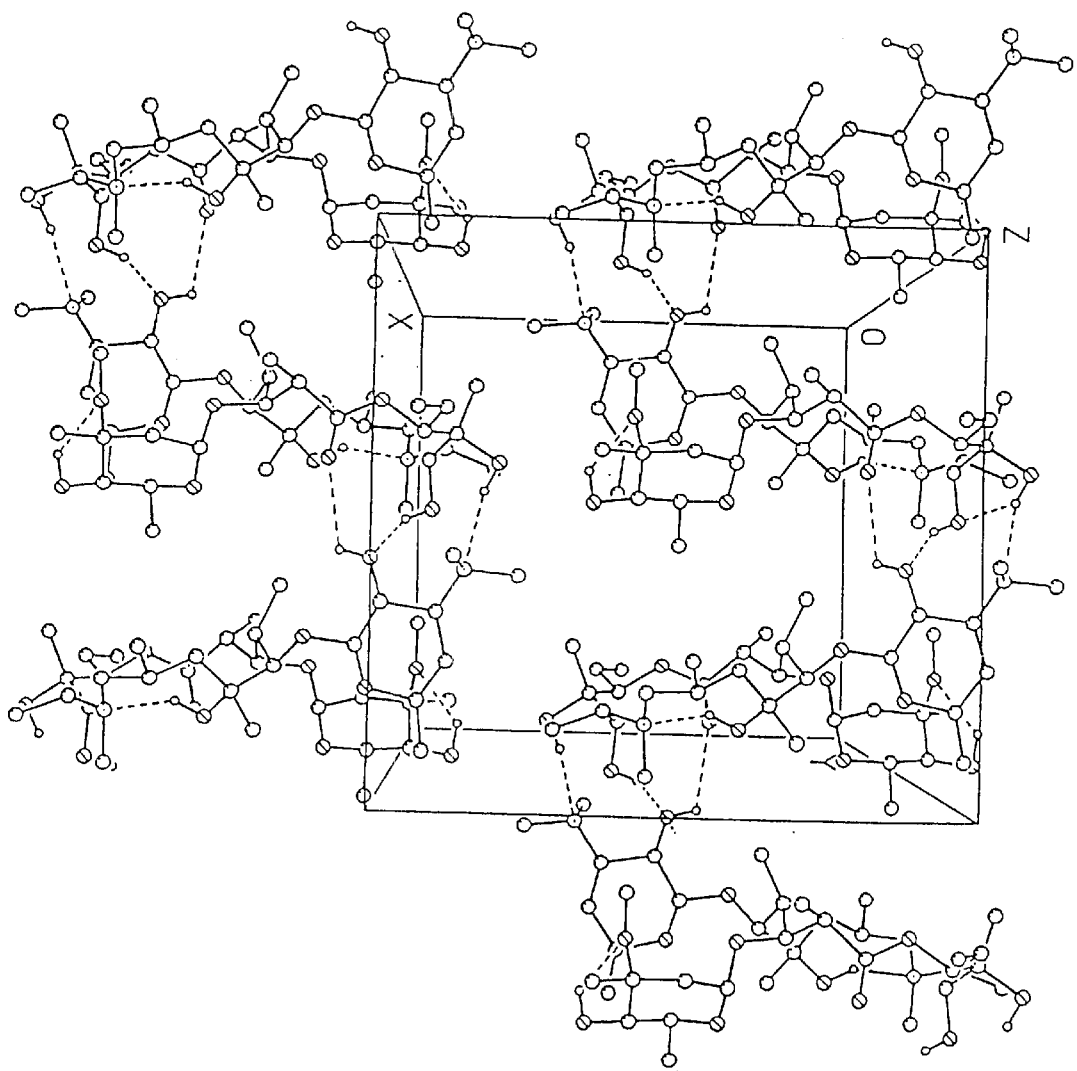
FIG. 9 depicts the molecular packing of the crystalline anhydrous azithromycin of the invention.

Based on the physical characteristics identified for the new crystal, we conclude that the new physical form is clearly different in its physical properties from the types of azithromycin patented to date. In order to confirm this conclusion, the structure was elucidated by single crystal X-ray diffraction, finding that it coincides with the anhydrous crystalline form, with a tetragonal crystal system and the space group P4$_2$2$_1$2. These and other crystallographic data from the diffraction analysis are compared with data reported for the dihydrated crystalline form in Table 1 (J. Chem. Res. 152–153 (1998)). FIG. 8 shows the molecular structure of the anhydrous crystalline azithromycin, and FIG. 9 illustrates the corresponding molecular packing.

TABLE 1

CRYSTALLOGRAPHIC DATA FOR THE CRYSTALLINE FORM AND COMPARISON WITH DATA REPORTED FOR THE DIHYDRATED CRYSTALLINE FORM OF AZITHROMYCIN.

| CRYSTAL SYSTEM | ANHYDROUS TETRAGONAL | DIHYDRATED ORTHORHOMBIC |
|---|---|---|
| SPACE GROUP | $P4_22_12$ | $P2_12_12_1$ |
| CELL CONSTANTS | A = 14.452 A$^0$ | a = 17.860 A$^0$ |
|  | B = 14.452 A$^0$ | b = 16.889 A$^0$ |
|  | C = 41.645 A$^0$ | c = 14.752 A$^0$ |
| Volume | 8698 A$^{03}$ | 4449.8 A$^{03}$ |
| Calculated density | 1.144 g/cm$^3$ | 1.177 g/cm$^3$ |
| λ (Cu-Kα) | 1.5418 A$^0$ | 1.5418 A$^0$ |
| Number of reflections | 3412 | 3846 |
| R | 0.0546 | 0.077 |

According to existing definitions (e.g. J. P. Glisker, Crystal Structure Analysis for Chemists and Biologists, VCH publishers, 1994, page 657, and H. G. Brittain, Physical Characteristics of Pharmaceutical Solids, Marcel Dekker, Inc., 1995, page. 108) the hydrated physical forms of azithromycin reported in U.S. Pat. No 4,474,768 and PCT/US87/01612 are pseudo-polymorphous forms of the anhydrous crystalline form obtained here, while the physical form reported by Kobrehel et al. (Yugoslav patent 592/81, Belgian patent 892357 U.S. Pat. No. 4,517,359, Mexican patent 9100364), according to patent PCT/US87/01612 corresponds to the amorphous form.

In addition to its novel features, the physical form obtained has physical characteristics that make it useful in preparing pharmaceutical preparations, with significant advantages over the forms existing to date. Thus, patent PCT/US87/0612 indicates that the forms reported by Kobrehel et al. (Yugoslav patent 592/81, Belgian patent 892357, U.S. Pat. No. 4,517,359, Mexican patent 9100364) and by Bright (U.S. Pat. No. 4,474,768) are highly hygroscopes, which significantly complicates the production of pharmaceutical preparations. In contrast, the anhydrous crystalline form obtained here, when exposed to room conditions, at an relative humidity average of 45%, for ten days, increases its moisture content by only 0.55%, while a reference sample of dihydrated azithromycin increased its moisture content by 1% in the same time. These data are indicative of anhydrous crystalline azithromycin's stability when exposed to moisture, which makes it useful in producing pharmaceutical preparations and represents a significant advantage over the more hygroscope forms.

In order to test the performance of anhydrous crystalline azithromycin in producing pharmaceutical preparations, 500 mg azithromycin tablets were made with total weight of one gram. The dissolution profile of these tablets was determined, and compared with the dissolution profile of tablets made with the same preparation using dihydrated azithromycin. The used solvents, and the procedure followed, were similar to those indicated for capsules in U.S. Pharmacopoeia 2000, page 186. The dissolution values obtained for the tablets made with anhydrous crystalline azithromycin were significantly higher than those obtained for the dihydrated form. This property gives the anhydrous crystalline form reported herein significant practical advantages over the dihydrated forms, given that increased solubility of the pharmaceutical preparation generally implies greater bioavailabilty of the drug and in consequence increases its therapeutic effectiveness.

The two characteristics described above for the anhydrous crystalline form, of its low hygroscope quality, and the fact that their pharmaceutical preparations have adequate dissolution, offering even higher solubility than the equivalent preparation using the dihydrated form, give the new crystalline form reported herein significant practical advantages over the forms of azithromycin reported to date.

Having described the invention, we consider it to constitute an innovation, and hereby claim the provisions of the following clauses:

1. A process for preparing azithromycin, comprising
    (a) treating erythromycin A with O-mesitylene sulfonyl hydroxylamine in the presence of sodium bicarbonate to produce 9-deoxo-6-deoxy-6,9-epoxy-9,9a-didehydro-9a-aza-homoerythromycin A; and
    (b) converting said 9-deoxo-6-deoxy-6,9-epoxy-9,9a-didehydro-9a-aza-homoerythromycin A into azithromycin.

2. A pharmaceutical composition, comprising crystalline anhydrous azithromycin and a pharmaceutically acceptable carrier.

3. The process for preparing azithromycin according to claim 1, wherein said treating comprises adding O-mesitylene sulfonyl hydroxylamine to a solution of erythromycin A in acetone.

4. The process for preparing azithromycin according to claim 1, wherein said converting comprises
    (b1) reacting said 9-deoxo-6-deoxy-6,9-epoxy-9,9a-didehydro-9a-aza-homoerythromycin A with hydrogen gas or sodium borohydride to form 9-deoxo-9a-aza-homoerythromycin A; and
    (b2) reacting said 9-deoxo-9a-aza-homoerythromycin A under Eschweiler-Clark conditions to form azithromycin.

5. The process for preparing azithromycin according to claim 3, wherein said solution is cooled to 0° C. prior to addition of O-mesitylene sulfonyl hydroxylamine.

6. The process for preparing azithromycin according to claim 1, further comprising recrystallizing said azithromycin from hexane.

7. Crystalline anhydrous azithromycin produced by the process of claim 6.

8. Crystalline anhydrous azithromycin.

9. Crystalline anhydrous azithromycin according to claim 8, having a melting point range of 188–189° C.

10. Crystalline anhydrous azithromycin according to claim 8, having an infrared absorption spectrum which includes absorption peaks at approximately 3600 cm$^{-1}$, approximately 3553 cm$^{-1}$, approximately 3375 cm$^{-1}$ and approximately 3075 cm$^{-1}$.

11. Crystalline anhydrous azithromycin according to claim 8, having a water content around 0.6% by weight.

12. Crystalline anhydrous azithromycin according to claim 8, which crystallizes in the space group $P4_22_12$.

13. Crystalline anhydrous azithromycin according to claim 8, having a crystal density of about 1.144 g/cm$^3$.

14. A pharmaceutical composition according to claim 2, in the form of a tablet.

* * * * *